(12) United States Patent
Adem et al.

(10) Patent No.: US 10,689,374 B1
(45) Date of Patent: Jun. 23, 2020

(54) PYRIMIDINE-THIAZOLIDINONE DERIVATIVES

(71) Applicant: UNITED ARAB EMIRATES UNIVERSITY, Al Ain (AE)

(72) Inventors: Abdu Adem, Al Ain (AE); Shaikha S. Al Neyadi, Al Ain (AE); Ibrahim M. Abdou, Al Ain (AE); Alaa A. Salem, Al Ain (AE); Naheed Amir, Al Ain (AE)

(73) Assignee: United Arab Emirates University, Al-Ain (AE)

( * ) Notice: Subject to any disclaimer, the term of this patent is extended or adjusted under 35 U.S.C. 154(b) by 0 days.

(21) Appl. No.: 16/510,198

(22) Filed: Jul. 12, 2019

(51) Int. Cl.
*C07D 277/34* (2006.01)
*C07D 417/12* (2006.01)

(52) U.S. Cl.
CPC ......... *C07D 417/12* (2013.01); *C07D 277/34* (2013.01)

(58) Field of Classification Search
CPC .. C07D 417/06; C07D 417/12; C07D 277/34; C07D 403/06
See application file for complete search history.

(56) References Cited

U.S. PATENT DOCUMENTS

| | | | |
|---|---|---|---|
| 6,521,610 B2 * | 2/2003 | Tiebes | A01N 43/76 514/183 |
| 6,528,512 B1 | 3/2003 | Gallagher et al. | |
| 7,001,910 B1 | 2/2006 | Mourelle Mancini et al. | |
| 7,396,836 B2 | 7/2008 | Harada et al. | |
| 2003/0134862 A1 | 7/2003 | Beierlein et al. | |
| 2004/0214872 A1 * | 10/2004 | Suto | A61K 31/41 514/369 |
| 2018/0258102 A1 * | 9/2018 | Shook | C07D 498/08 |
| 2019/0192535 A1 * | 6/2019 | Shook | A61K 39/395 |

FOREIGN PATENT DOCUMENTS

| | | | | |
|---|---|---|---|---|
| FR | 2856401 A1 | 12/2004 | | |
| WO | WO-2004093803 A2 * | 11/2004 | ........... | A61K 31/425 |

OTHER PUBLICATIONS

J. Wagner et al., 55 Canadian Journal of Chemistry, 4028-4036 (1977) (Year: 1977).*
R. Hull, Journal of the Chemical Society, 4845-4857 (1957) (Year: 1957).*
E.C. Taylor et al., 80 Journal of the American Chemical Society, 427-431 (1958) (Year: 1958).*
CAS Abstract RN 343375-26-8 (2001) (Year: 2001).*
Imran, Mohd, Baber Ilyas, and Suroor Ahmad Khan. "Recent thiazolidinediones as antidiabetics." Journal of Scientific and Industrial Research 66.2 (2007): 99.
Liu, Xiaofeng, et al. "Discovery and SAR of thiazolidine-2, 4-dione analogues as insulin-like growth factor-1 receptor (IGF-1R) inhibitors via hierarchical virtual screening." Journal of medicinal chemistry 53.6 (2010): 2661-2665.
Aneja, Deepak K., et al. "Synthesis of new pyrazolyl-2, 4-thiazolidinediones as antibacterial and antifungal agents." Organic and medicinal chemistry letters 1.1 (2011): 1-11.

* cited by examiner

*Primary Examiner* — Alexander R Pagano
(74) *Attorney, Agent, or Firm* — Richard C. Litman; Nath, Goldberg & Meyer (57) ABSTRACT

Pyrimidine-thiazolidinone derivatives may be used for preventing or treating diseases in humans or animals, and have demonstrated efficacy specifically in treating type-2 diabetes. Methods of synthesizing the pyrimidine-thiazolidinone derivatives, described herein, can provide high yields in a short time and with high purity. The pyrimidine-thiazolidinone derivatives demonstrate improved hypoglycemic activity compared to most anti-diabetic drugs currently available.

11 Claims, 11 Drawing Sheets

105b-d
105b: X = N-CH₃, Ar = 2,4-Diaminopyrimidine (78%)
105c: X = O, Ar = 2,4-Diaminopyrimidine (84%)
105: X = O, Ar = 2-Chloro-4-aminopyrimidine (75%)

112, 89%

119, 72%

126, 81%

130a-g

130a: R = N,N-dimethylamine, R₁ = H (89%)
130b: R = NH₂, R₁ = H (87%)
130c: R = N,N-dimethylamine, R₁ = CH₂COOH (81%)
130d: R = isopropyl, R₁ = CH₂COOH (86%)
130e: R = N-morpholine, R₁ = CH₂COOH (88%)
130f: R = n-propylamine, R₁ = CH₂COOH (83%)
130g: R = Benzylamine, R₁ = CH₂COOH (84%)

134a-c

134a: R = 4-chloroaniline, (80%)
134b: R = N-morpholine, (82%)
105: R = n-propylamine, (76%)

105b: X = N-CH₃, Ar = 2,4-Diaminopyrimidine (78%)
105c: X = O, Ar = 2,4-Diaminopyrimidine (84%)
105d: X = O, Ar = 2-Chloro-4aminopyrimidine (75%)

PYRIMIDINE-THIAZOLIDINONE DERIVATIVES

BACKGROUND

1. Field

The disclosure of the present patent application relates to novel pyrimidine-thiazolidinone derivatives, their synthesis, and their use as anti-diabetic agents for treating type-2 diabetes by inhibiting basal insulin and increasing glucose stimulated insulin.

2. Description of the Related Art

Increasing incidence of diabetes is considered to be one of the most common concerns in the medical field today. Diabetes is one of the most common diseases. In the U.S. alone, in 2015, over 30 million Americans aged 18 years or older were estimated to have diagnosed or undiagnosed diabetes—about 12.2% of the adult population. Of these, about 23 million—or about 9.3%—were estimated to have been diagnosed with diabetes. See National Diabetes Statistical Report, 2017, "Estimates of Diabetes and Its Burden in the United States," at http://wwvv.diabetes.org/assets/pdfs/basics/cdc-statistics-report-2017.pdf. About 90% to 95% of those with diabetes have type 2 diabetes; only about 5% to 10% have type 1 diabetes. Id.

As a result, there is an increasing demand for novel compounds that have good potency, with fewer side effects, in treating patients for diabetes. Peroxisome proliferator-activated receptors (PPARs) are ligand-activated transcription factors regulating the expression of genes involved in lipid and glucose metabolism.

There are three isotypes of PPARs. PPARα is expressed mainly in the liver, and is involved in fatty acid catabolism. PPARβ (also known as PPARδ) is expressed in many parts of the body, and is associated with fatty acid oxidation. PPARγ is involved in glucose metabolism, and is the most studied for drug discovery.

PPARγ was identified as a key regulator of adipogenesis, and it also plays an important role in type 2 diabetes, cellular differentiation, insulin sensitization, atherosclerosis and cancer. A class of high-affinity PPARγ synthetic ligands includes the anti-diabetic thiazolidinedione (TZD) drugs, such as troglitazone, rosiglitazone, pioglitazone and ciglitazone. Rosiglitazone and pioglitazone are currently marketed PPARγ activators used to treat type 2 diabetes to reduce hyperglycemia by promoting insulin action without additional insulin secretion.

SUMMARY

Pyrimidine-thiazolidinone derivatives may be used for preventing or treating diseases in humans or animals, and have demonstrated efficacy specifically in treating type-2 diabetes. Methods of synthesizing the pyrimidine-thiazolidinone derivatives, described herein, can provide high yields in a short time and with high purity. The pyrimidine-thiazolidinone derivatives demonstrate improved hypoglycemic activity compared to most anti-diabetic type-2 drugs currently available, such as pioglitazone. The compounds are more potent than conventional drugs. As such, the compounds can be used in lower doses and, hence, have less side effects.

These and other features of the present findings will become readily apparent upon further review of the following specification.

BRIEF DESCRIPTION OF THE DRAWINGS

FIG. 7 depicts the synthesis scheme for compounds 103, 104, and 105a.

Similar reference characters denote corresponding features consistently throughout the attached drawings.

DETAILED DESCRIPTION OF THE PREFERRED EMBODIMENTS

Pyrimidine-thiazolidinone derivatives may be used for preventing or treating diseases in humans or animals, and have demonstrated efficacy specifically in treating type-2 diabetes. According to an embodiment, the pyrimidine-thiazolidinone derivatives can bind and activate Peroxisome Proliferator-Activated Receptors Gamma (PPARγ) and enhance insulin sensitivity

The pyrimidine-thiazolidinone derivatives may be synthesized in high yields, with high purity. The pyrimidine-thiazolidinone derivatives can be effective in decreasing blood sugar. These compounds may be administered to a patient in any suitable pharmaceutical formulation, with any suitable pharmaceutical excipients known in the industry, for administration to a patient in any suitable manner as generally known in the industry that may be determined or selected by the medical practitioner treating the patient.

Figure 1:
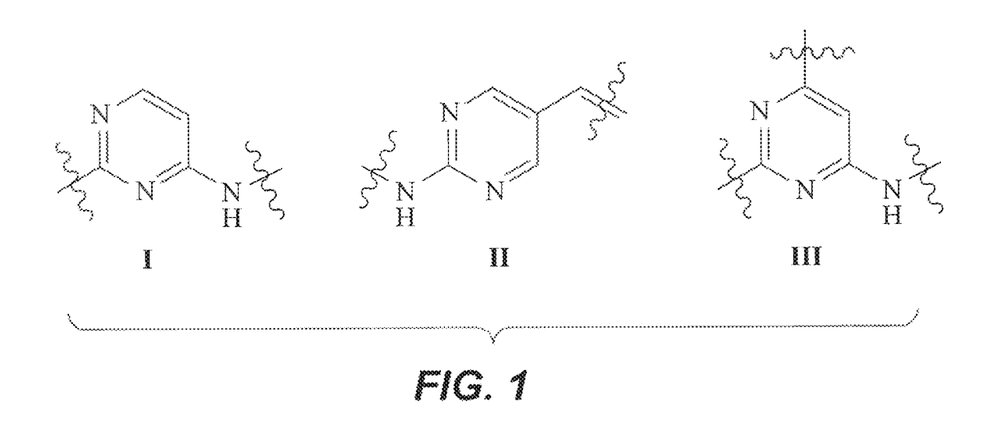
FIG. 1 depicts mono, di- and tri-substituted pyrimidines, structures I, II, and III, according to an embodiment of the present disclosure.

According to an embodiment, the pyrimidine-thiazolidinone derivatives include mono, di- and tri-substituted pyrimidines, as shown in FIG. 1 (structures I, II, and III).

Figure 2:
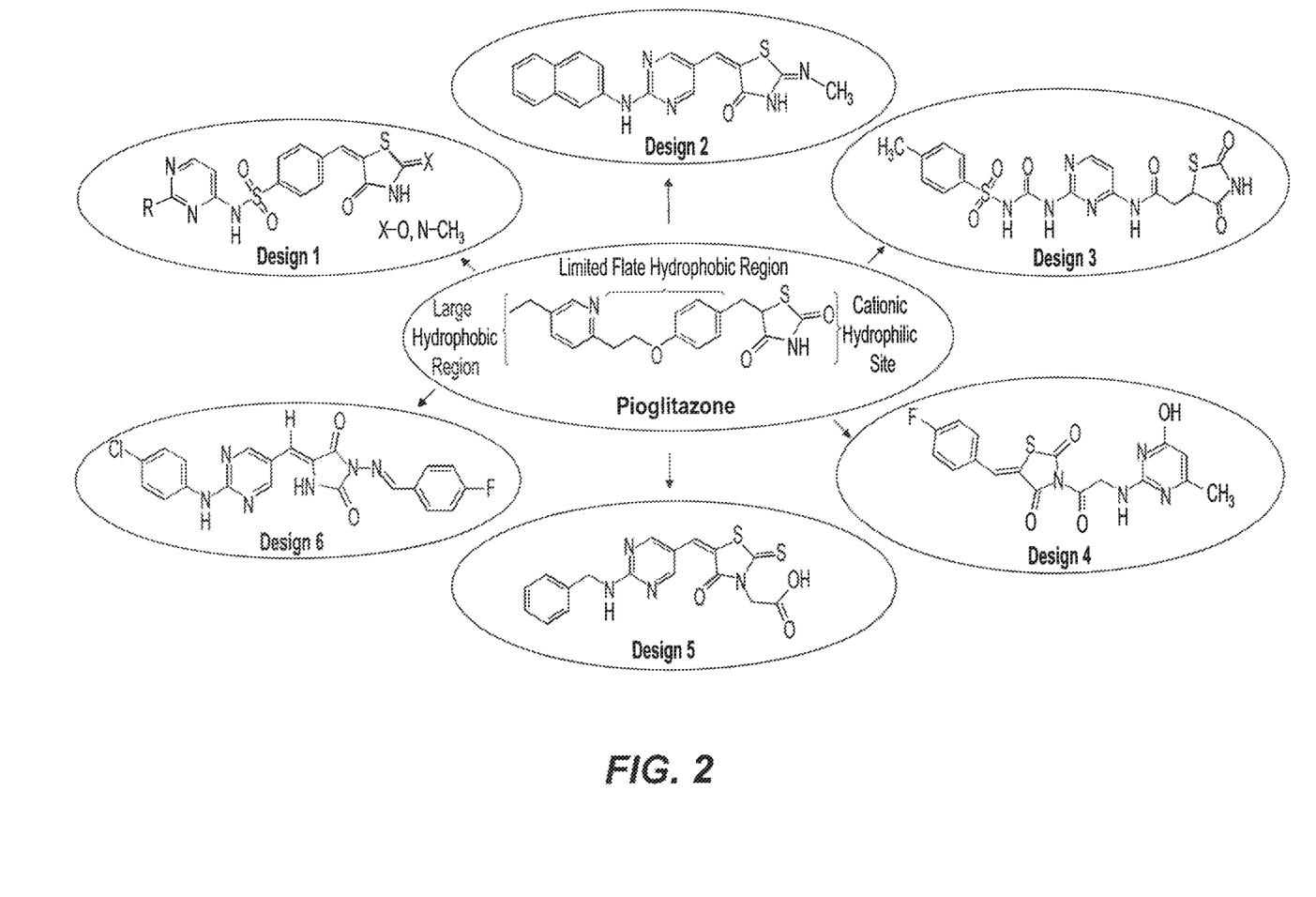
FIG. 2 depicts pyrimidine-thiazolidinone backbone structures according to an embodiment of the present disclosure.

According to an embodiment, the pyrimidine-thiazolidinone derivatives includes pioglitazone-derived structures, as shown in FIG. 2.

Figure 6:
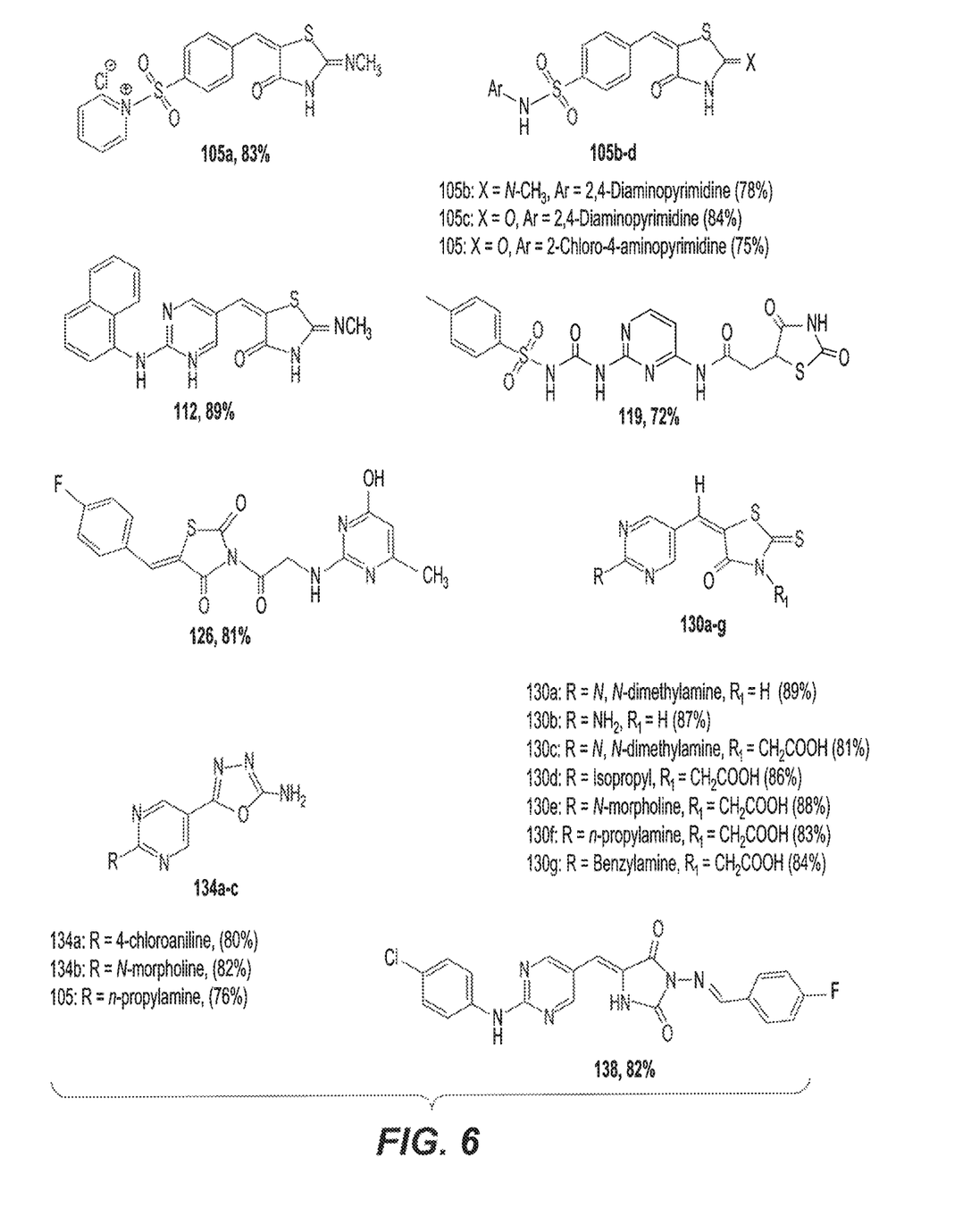
FIG. 6 lists the structures of compounds 105a-d, 112, 119, 126, 134a-c, 130a-g, and 138.

According to an embodiment, the pyrimidine-thiazolidinone derivatives include thiazolidinedione-2,4-dione, such as compounds 105a-d, 112, 117, 119, 121, 126 or a pharmaceutically acceptable salt thereof (FIG. 6) and rhodanine-pyrimidine derivatives, such as compounds 130a, 130b, 130c, 130d, 130e, 130f, 130g, or a pharmaceutically acceptable salt thereof (FIG. 6).

According to an embodiment, the pyrimidine-thiazolidinone derivatives include at least one of:

105a

105b

126 a pharmaceutically acceptable salt thereof.

As described herein, in-vitro studies revealed that compounds 105a, 105b and 126 showed both a significant decrease of basal insulin secretion and an increase of glucose stimulated insulin release from βTC6 cells. Accordingly, compounds 105a, 105b and 126 can inhibit basal insulin secretion and thereby prevent hypoglycemia, while also being able to increase glucose-stimulated insulin secretion in the presence of glucose, and thereby prevent hyperglycemia.

The present findings are illustrated by the following examples.

Example 1

Figure 3A:
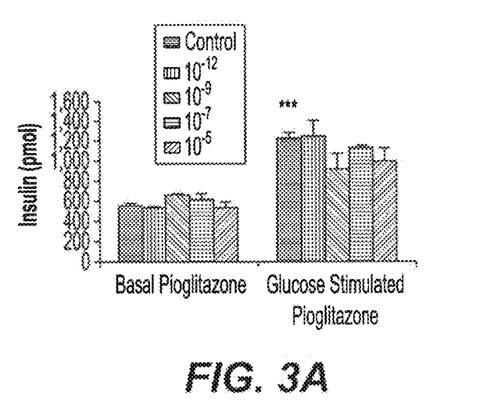
FIG. 3A is a graph showing the effect of pioglitazone on insulin secretion both in the absence and presence of 2.8 mM glucose from βTC6 cells.

Effects of New Thiazolidinedione-2,4-dione- and Rhodanine-Pyrimidines on Insulin Secretion from βTC6 Cell Line Secretion of insulin by βTC6 cells was measured using the high range insulin Sandwich ELISA kit. FIG. 3A shows the effect of pioglitazone on insulin secretion in the presence and absence of 2.88 mM glucose. As can be seen from FIG. 3A, pioglitazone (at $10^{-12}$, $10^{-9}$, $10^{-7}$, and $10^{-5}$ M concentrations) did not show any significant effect on basal or glucose stimulated insulin secretion.

Figure 3B:
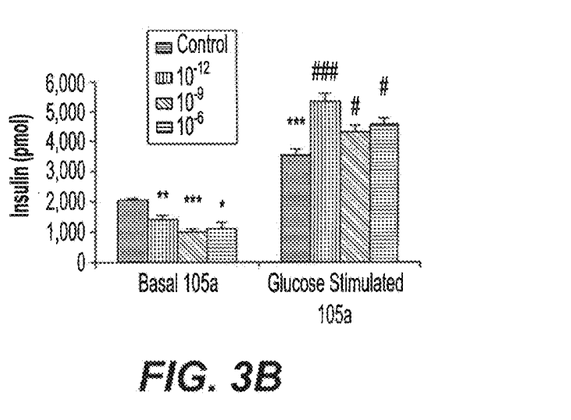
FIG. 3B is a graph showing the effect of compound 105a on insulin secretion both in the absence and presence of 2.8 mM glucose from βTC6 cells.
Figure 3C:
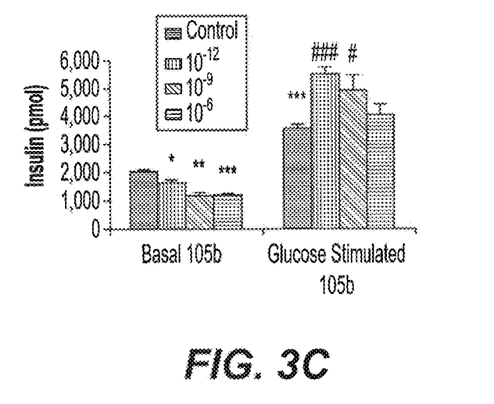
FIG. 3C is a graph showing the effect of compound 105b on insulin secretion both in the absence and presence of 2.8 mM glucose from βTC6 cells.
Figure 3D:
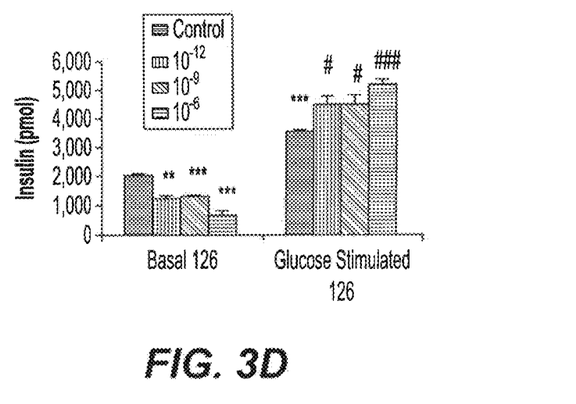
FIG. 3D is a graph showing the effect of compound 126 on insulin secretion both in the absence and presence of 2.8 mM glucose from βTC6 cells.

Similarly, a variety of thiazolidinedione-2,4-dione-pyrimidine derivatives, at $10^{-12}$, $10^{-9}$, $10^{-6}$ M concentrations, were investigated for their effect on insulin secretion in the absence and presence of 2.8 mM glucose from βTC6 cells. Certain compounds did not show any effect on the secretion of insulin in the absence, or in the presence of glucose. Compounds 105a, 105b and 126 showed significant decrease of basal insulin secretion and significant increase of glucose stimulated insulin release from βTC6 cells (FIGS. 3B-3D). These compounds inhibit basal insulin secretion and, thereby, prevent hypoglycemic effect. These compounds also increase insulin secretion in the presence of glucose and, thereby, prevent hyperglycemia.

Figure 3E:
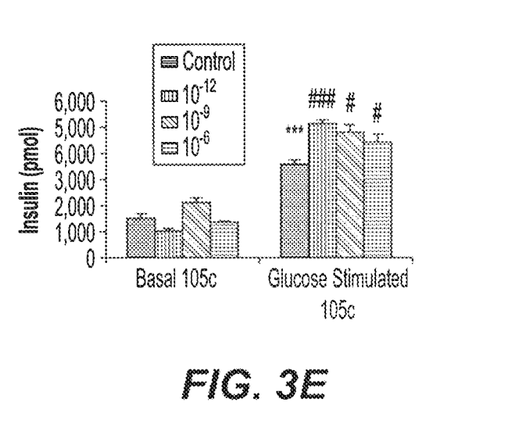
FIG. 3E is a graph showing the effect of compound 105c on insulin secretion both in the absence and presence of 2.8 mM glucose from βTC6 cells.
Figure 3F:
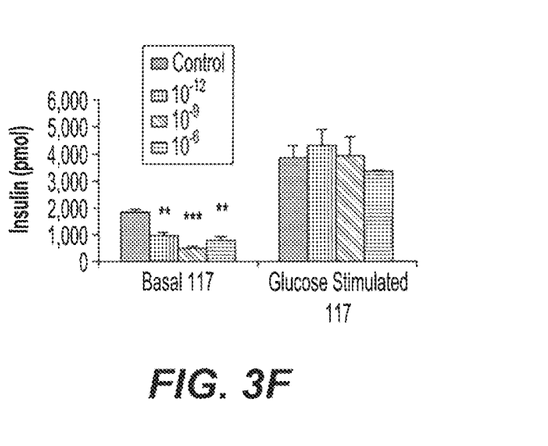
FIG. 3F is a graph showing the effect of compound 117 on insulin secretion both in the absence and presence of 2.8 mM glucose from βTC6 cells.
Figure 3G:
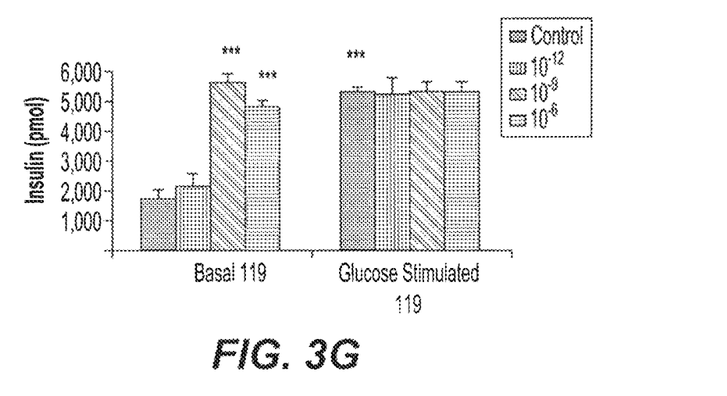
FIG. 3G is a graph showing the effect of compound 119 on insulin secretion both in the absence and presence of 2.8 mM glucose from βTC6 cells.

Compound 105c had no effect on basal insulin release but significantly increased glucose stimulated insulin release (FIG. 3E). Compounds 117 and 119 showed opposing results—compound 117 significantly inhibited basal insulin release, while compound 119 significantly increased basal insulin release (FIGS. 3F and 3G).

Accordingly, these results support the conclusion that compounds 105a, 105b and 126 are the most potent thiazolidinedione-2,4-dione-pyrimidine derivatives for both inhibiting basal insulin and increasing glucose-stimulated insulin secretion. These compounds are more potent than pioglitazone. Accordingly, the compounds can be administered at lower concentrations and, hence, have less side effects.

The effects of rhodanine-pyrimidine derivatives 130a-g were also investigated at $10^{-12}$, $10^{-9}$, $10^{-6}$ M concentrations, for effect on insulin secretion in absence and presence of 2.8 mM glucose in βTC6 cells. The results are provided in FIGS. 4A-4E.

Compounds 130a and 130d did not show any effect (results not shown).

Figure 4A:
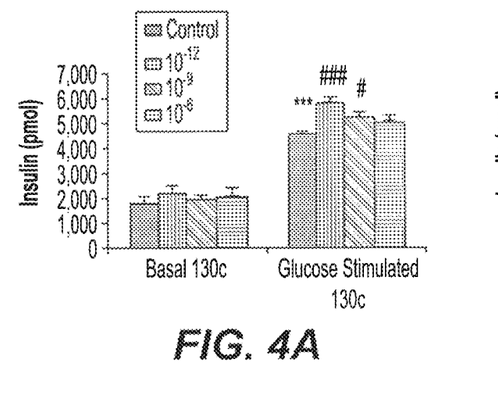
FIG. 4A is a graph showing the effect of compound 130c on insulin secretion both in the absence and presence of 2.8 mM glucose from βTC6 cells.
Figure 4B:
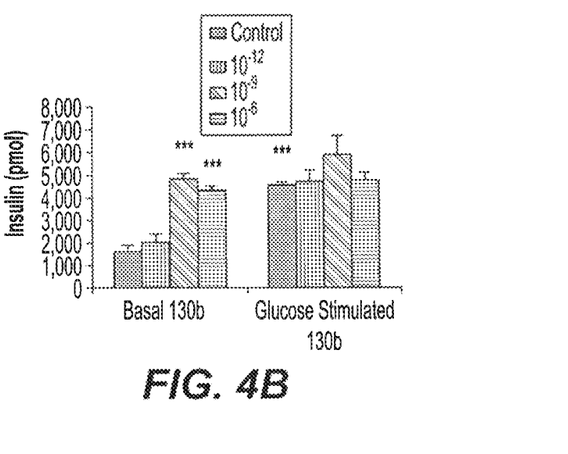
FIG. 4B is a graph showing the effect of compound 130b on insulin secretion both in the absence and presence of 2.8 mM glucose from βTC6 cells.
Figure 4C:
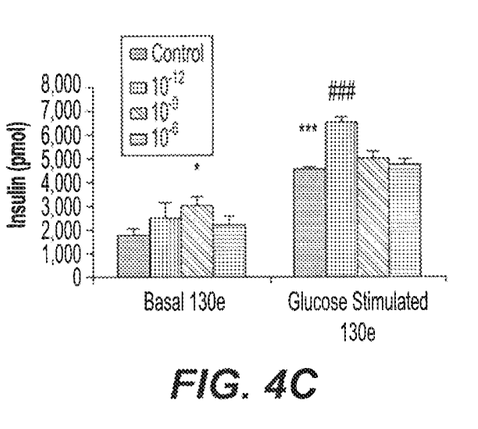
FIG. 4C is a graph showing the effect of compound 130e on insulin secretion both in the absence and presence of 2.8 mM glucose from βTC6 cells.
Figure 4D:
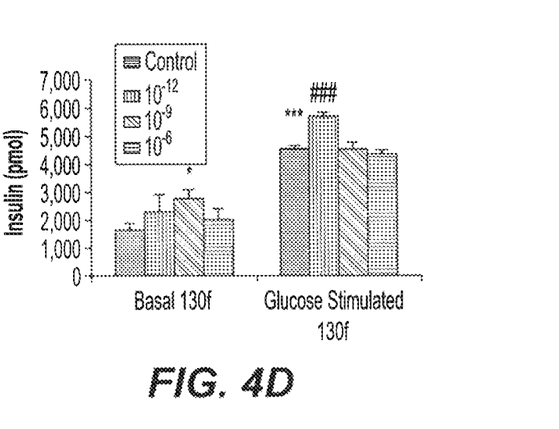
FIG. 4D is a graph showing the effect of compound 130f on insulin secretion both in the absence and presence of 2.8 mM glucose from βTC6 cells.
Figure 4E:
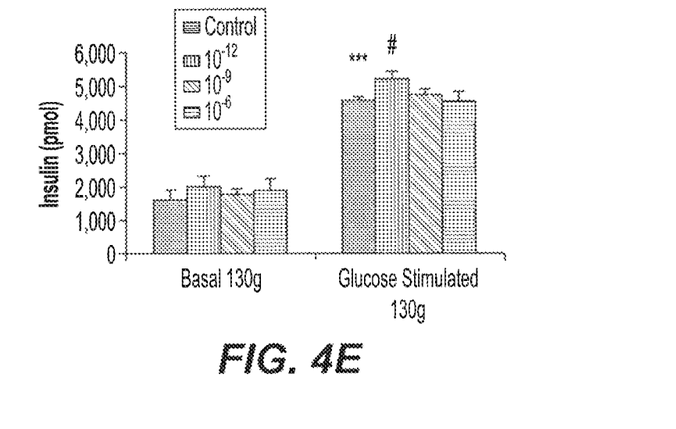
FIG. 4E is a graph showing the effect of compound 130g on insulin secretion both in the absence and presence of 2.8 mM glucose from βTC6 cells.

Compounds 130c and 130g significantly increased glucose-stimulated insulin release, while compound 130b significantly increased only basal insulin release (FIGS. 4A, 4E and 4B). The most potent of the rhodanine-pyrimidine derivatives, compounds 130e and 130f, demonstrate significant increases in both basal and glucose-stimulated insulin release (FIGS. 4C and 4D).

Example 2

Glucose Uptake Assay

Figure 5A:
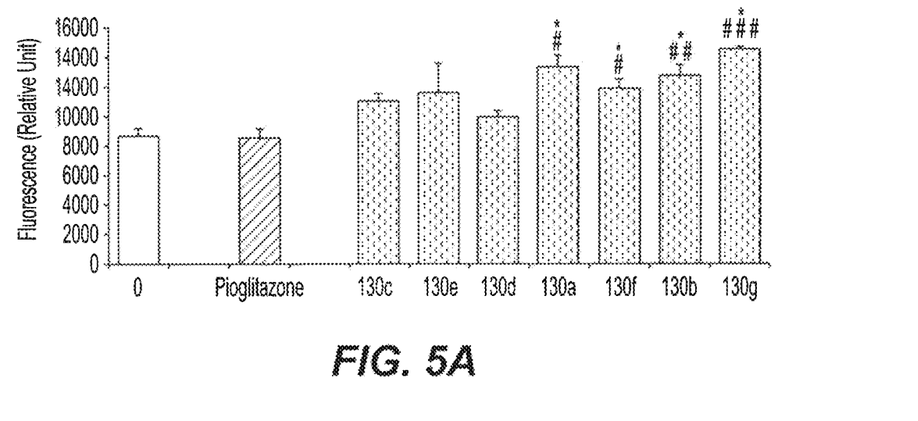
FIG. 5A is a bar graph comparing the results of pioglitazone with compounds 130a-g, each at a concentration of 10 μM, for effect on glucose uptake from β TC6 cells.
Figure 5B:
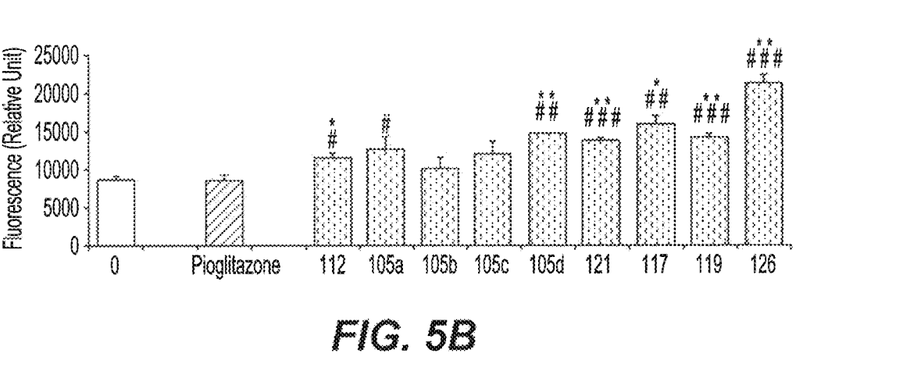
FIG. 5B is a bar graph comparing the results of pioglitazone with compounds 112, 105a-d, 121, 117, 119, and 126, each at a concentration of 10 μM, for effect on glucose uptake from β TC6 cells.
Figure 5C:
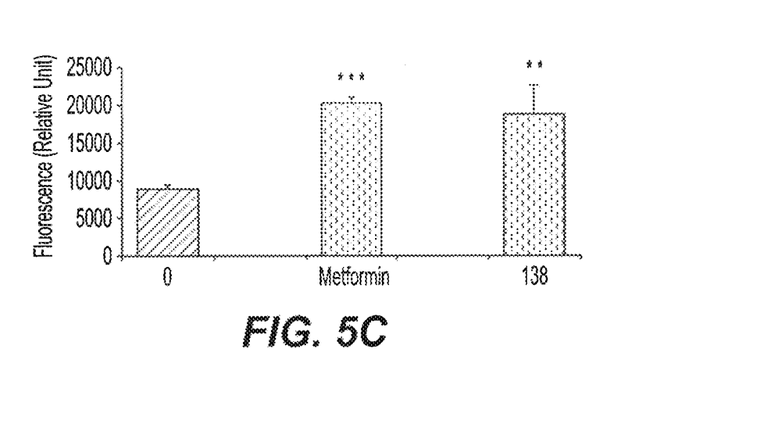
FIG. 5C is a bar graph comparing the results of metformin with compound 138, each at a concentration of 10 μM, for effect on glucose uptake from β TC6 cells.

The results of the in vitro glucose uptake study are depicted in FIGS. 5A-5C. The results indicate that compounds 130e, 130f, 130g, 112, 105a, 105b, 105c, 117, and 119 demonstrate the most potent activity among the glitazones studied here. Compounds 130g and 126 demonstrated the most potency, enhancing the glucose uptake significantly ($p<0.001$) (FIGS. 5A to 5C).

The structures of compounds 105a-d, 112, 119, 126, 134, 130a-g, and 138 are depicted in (FIG. 6).

Example 3

Synthesis of Novel Pyrimidine-Thiazolidinone Derivatives

Thiazolidine-2,4-dione 101: A mixture of monochloroacetic acid (10.58 mmol, 1.00 g) and thiourea derivatives (10.60 mmol, 0.81 g) in water (2 ml) were introduced into a CEM microwave reaction vessel and irradiated at 140° C. for 10 min. The solid was filtered and recrystallized from hot water to yield 1.10 g (90%) of thiazolidinone 101, m.p. 124-125° C.; IR (KBr, cm$^{-1}$): 1241 (CN), 1492 (CH$_2$), 1666, 1738 (C═O), 3121 (NH); $^1$H-NMR [CDCl$_3$, 400 MHz]: (δ, ppm) 4.20 (s, 2H, CH$_2$), 9.10 (bs, 1H, NH); $^{13}$C-NMR [CDCl$_3$, 100 MHz]: (δ, ppm) 35.9, 168.5, 169.2.

5-Benzylidene-2,4-thiazolidinedione 103: A mixture of benzaldehyde 102 (0.188 mmol, 0.020 g) and 2,4-thiazolidinedione 101 (0.188 mmol, 0.022 g) in dry toluene (3 ml) was placed in a 10.0 mL CEM-microwave vial. To the above mixture, a few drops of piperidine were added and the reaction mixture was irradiated at 135° C. for 10-15 min. On cooling, the solid precipitated was filtered and washed with dry ethanol to yield 103 (94%, m.p 242° C.).

Figure 7:
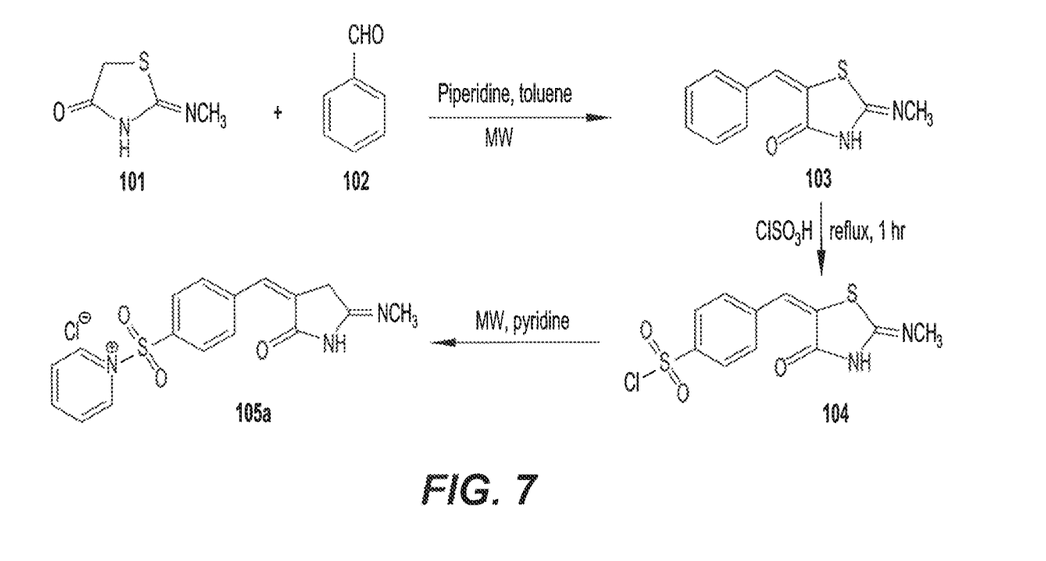

4'-Chlorosulphonylbenzylidene-2,4-thiazolidinedione 104: Benzylidene-2,4-thiazol-idinedione 103 (0.0388 mole, 8.0 g) was placed in a 100 ml round bottom flask equipped with a condenser and dropping funnel. Chlorosulphonic acid (0.155 mole, 18.08 g) was added at room temperature and the reaction mixture was heated for 1 h on a water bath. The reaction mixture was cooled and poured into crushed ice. The solid was filtered and dried to yield 104 (66%, m.p 181° C.). The synthetic scheme for production of compounds 103 and 104 is set out in FIG. 7.

2-(Methylimino)-5-[4'-(N-pyridinesulfonyl)benzylidine] thiazolidin-4-one chloride salt 105a: A mixture of p-chlorosulphonyl benzylidene-2,4-thiazolidinedione 104 (0.1 mmol, 0.03 g) and 3.0 ml of pyridine was heated under microwave irradiation at 100° C. for 10 min, the reaction mixture was then poured into 20.0 ml of ice-water and the solid obtained was filtered and recrystallized from ethanol. This compound was gray powder, yield 83%; mp 280-281° C.; IR (KBr, cm$^{-1}$): 3487 (NH TZD), 3067 (C—H, aromatic), 1683 (C═O), 1486 (C═N); $^1$H-NMR [DMSO-d$_6$, 400 MHz]: (δ, ppm) 3.08 (s, 3H, CH$_3$), 3.40-3.42 (m, 1H, NH, exchanges with D$_2$O), 7.56 (d, 2H, aromatic H, J=8.2 Hz), 7.69 (d, 2H, aromatic H, J=8.2 Hz), 7.88 (s, 1H, CH), 7.97 (t, 2H, pyridine, J=7.2 Hz), 8.49 (t, 1H, pyridine, J=7.4 Hz), 8.87 (d, 2H, pyridine, J=5.1 Hz); $^{13}$C-NMR [DMSO-d$_6$, 100 MHz]: (δ, ppm) 28.2 (CH$_3$), 122.9 (C5-thiazolidionedione), 126.8, 127.4, 130.3, 132.3, 134.0, 142.7, 146.0 (aromatic C), 148.4 (CH carbons), 166.4 (C═N), 168.2 (C═O); Anal. Calcd for C$_{16}$H$_{14}$N$_3$O$_3$S$_2$: C, 53.32; H, 3.92; N, 11.66; S, 17.79; Found: 53.77; H, 3.99; N, 11.94; S, 18.07. The synthetic scheme for production of compound 105a is set out in FIG. 7.

N-(2'-Aminopyrimidin-4'-yl)-4-[2"-(methylimino)-4"-oxothiazolidin-5"-ylidene) methyl] benzene-sulfonamide 105b: A mixture of aromatic amine (0.1 mmol) and p-chlorosulphonyl benzylidene-2,4-thiazolidinedione 104 (0.1 mmol, 0.03 g) was added to DIPEA (0.5 ml in 3 ml ethanol). The mixture was heated under microwave irradiation at 100° C. for 10 min. The reaction mixture was then poured into 20.0 ml of ice-water and the solid obtained was filtered and recrystallized from ethanol as a light brown powder, yield 78%; mp 247-248° C.; IR (KBr, cm$^{-1}$): 3554, 3524 (NH$_2$), 3353 (NH TZD), 3029 (C—H aromatic), 1686 (C═O), 1519 (C═N); $^1$H-NMR [DMSO-d$_6$, 400 MHz]: (δ, ppm) 3.08 (s, 3H, CH$_3$), 5.98 (d, 1H, H5-pyrimidine, J=6.0 Hz), 7.56 (m, 2H, aromatic), 7.58 (1H, NH, exchanges with D$_2$O), 7.56 (d, 2H, aromatic H, J=8.0 Hz), 7.69 (d, 1H, H6-pyrimidine, J=6.0 Hz), 7.88 (s, 1H, olefinic H), 8.05 (bs, 2H, NH$_2$, exchanges with D$_2$O), 11.63 (bs, 1H, NH, exchanged with D$_2$O); $^{13}$C-NMR [DMSO-d$_6$, 100 MHz]: (δ, ppm) 53.9 (CH$_3$), 97.6 (C5-pyrimidine), 122.4 (C5-thiazolidionedione), 126.9, 130.2, 132.4, 133.4 (aromatic C), 142.7 (olefinic C), 150.3 (C4-pyrimidine), 155.6 (C═N), 165.4 (C6-pyrimidine), 166.3 (C2-pyrimidine), 167.9 (C═O); Anal. Calcd for C$_{15}$H$_{14}$N$_6$O$_3$S$_2$: C, 46.14; H, 3.61; N, 21.52; S, 16.43; Found: C, 46.59; H, 3.68; N, 21.80; S, 16.71.

(E)-N-(2'-Aminopyrimidin-4'-yl)-4-(2",4"-dioxothiazolidin-5"-ylidene)methyl) benzene-sulfonamide 105c: Light brown powder, yield 84%; mp 299° C.; IR (KBr, cm$^{-1}$): 3513, 3476 (NH$_2$), 3353 (NH), 3130 (C—H aromatic), 1675 (C═O), 1450 (C═C); $^1$H-NMR [DMSO-d$_6$, 400 MHz]: (δ, ppm) 4.33 (bs, 1H, NH, exchanges with D$_2$O), 5.84 (d, 1H, H5-pyrimidine, J=6.0 Hz), 6.49 (bs, 2H, NH$_2$, exchanges with D$_2$O), 7.11 (m, 2H, aromatic), 7.36 (d, 2H, aromatic H, J=8.0 Hz), 7.60 (d, 2H, H6-pyrimidine, J=6.0 Hz), 7.88 (s, 1H, olefinic H), 11.65 (bs, 1H, NH, exchanges with D$_2$O); $^{13}$C-NMR [DMSO-d$_6$, 100 MHz]: (δ, ppm) 96.7 (C5-pyrimdine), 122.9 (C5-thiazolidion), 126.8, 127.4, 132.3, 134.0 (aromatic C), 142.7 (olefinic C), 152.6 (C4-pyrimidine), 158.6 (C6-pyrimidine), 163.2 (C2-pyrimidine), 165.0 (C═O), 168.2 (C═O); Anal. Calcd for C$_{14}$H$_{11}$N$_5$O$_4$S$_2$: C, 44.56; H, 2.94; N, 18.56; S, 16.99; Found: C, 45.01; H, 3.01; N, 18.84; S, 17.27.

Figure 8:
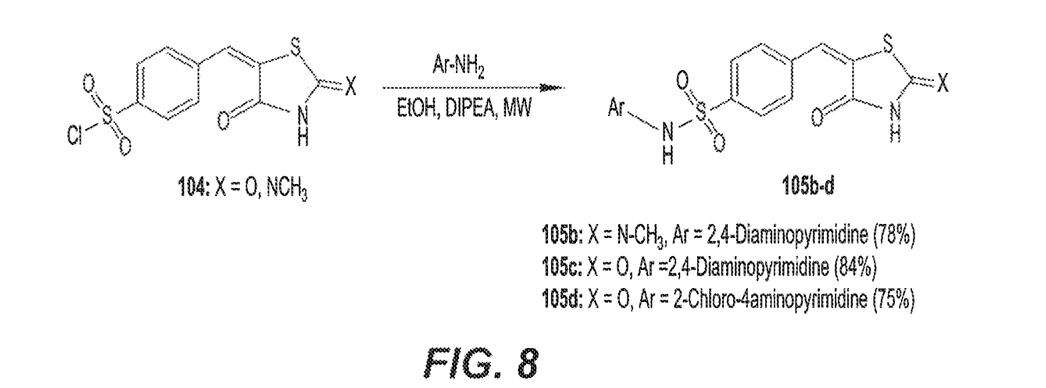
FIG. 8 depicts the synthetic scheme for compounds 105b-d.

(E)-N-(2'-Chloropyrimidin-4'-yl)-4-(2",4"-dioxothiazolidin-5"-ylidene)methyl) benzene-sulfonamide 105d: Pale yellow powder, yield 75%; mp 312° C.; IR (KBr, cm-1): 3431 (NH TZD), 3249 (NH-sec.amine linkage), 3077 (C—H, aromatic), 1698 (C═O), 1491 (C═N); $^1$H-NMR [DMSO-d$_6$, 400 MHz]: (δ, ppm) 5.87 (d, 1H, H5-pyrimidine, J=7.0 Hz), 7.10 (d, 2H, aromatic, J=8.0 Hz), 7.18 (d, $^1$H, H6-pyrimidine, J=7.0 Hz), 7.26 (d, 2H, aromatic, J=8.0 Hz), 7.31 (s, 1H, olefinic H), 8.34 (b, NH, exchanges with D$_2$O), 11.91 (bs, 1H, NH, exchanges with D$_2$O); $^{13}$C-NMR [DMSO-d$_6$, 100 MHz]: (δ, ppm) 99.8 (C5-pyrimdine), 119.8 (C5-thiazolidionedione), 127.1, 128.3, 133.0, 134.7 (aromatic C), 141.5 (olefinic C), 152.4 (C4-pyrimidine), 158.6 (C6-pyrimidine), 163.9 (C2-pyrimdine), 165.0 (C=O), 169.1 (C=O); Anal. Calcd for C$_{14}$H$_9$ClN$_4$O$_4$S$_2$: C, 42.37; H, 2.29; N, 14.12; S, 16.16; Found: C, 42.82; H, 2.36; N, 14.40; S, 16.44. The synthetic scheme for production of compounds 105b, 105c, and 105d is set out in FIG. 8.

Figure 9:
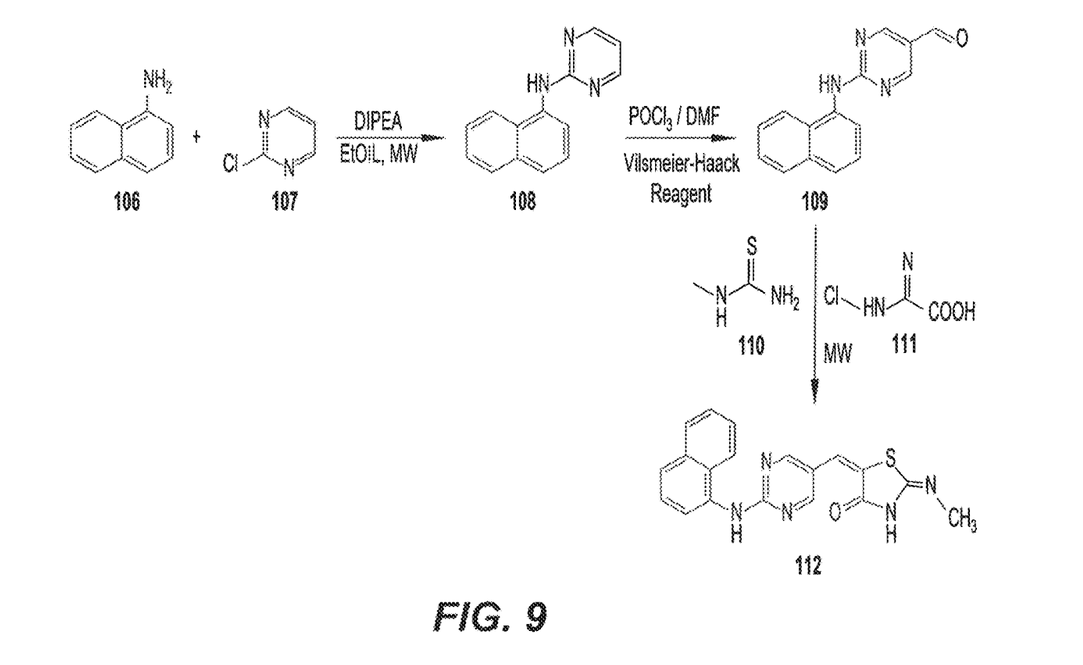
FIG. 9 depicts the synthetic scheme for compounds 108, 109, and 112.

(E)-2-(Methylimino)-5-[2'-(naphthalen-1"-ylamino)pyrimidin-5'-yl]methylene) thiazol-idin-4-one 112: A mixture of N-methylthiourea 110 (3.0 mmol, 0.27 g), chloroacetic acid 111 (3.6 mmol, 0.2 ml) and aldehyde 109 (3.0 mmol, 0.74 g) was heated under microwave irradiation at 90-110° C. for 10-20 min. After cooling to room temperature; the reaction mixture was extracted with CH$_2$Cl$_2$. The organic layer washed with aqueous NaHCO$_3$ and water then dried over anhydrous Na$_2$SO$_4$. The solvent was removed under vacuum and the residue was recrystallized from EtOH/water to give 112 as pale yellow powder with yield 89%; mp 296-297° C.; IR (KBr, cm$^{-1}$): 3428 (NH TZD), 3263 (NH-see.amine linkage), 3000 (C—H, aromatic), 1685 (C=O), 1471 (C=N); $^1$H-NMR [DMSO-d$_6$, 400 MHz]: (δ, ppm) 3.09 (s, 3H, CH$_3$), 7.59 (s, 1H, olefinic H), 7.64 (m, 2H, naphthalene), 7.97 (s, 1H, NH, exchanges with D$_2$O), 8.06-8.11 (m, 3H, naphthalene), 8.49 (s, 1H, naphthalene), 9.09 (s, 2H, H4,6-pyrimidine), 9.14 (m, 1H, naphthalene), 9.77 (bs, 1H, NH, exchanges with D$_2$O); $^{13}$C-NMR [DMSO-d$_6$, 100 MHz]: (δ, ppm) 31.5 (CH$_3$), 122.7 (C5-pyrimidine), 124.9 (C4-thiazolidionedione), 126.9, 127.3, 128.1, 128.3, 128.9, 128.93, 129.6, 132.6, 133.2, 134.2 (naphthelene C), 134.8 (olefinic C), 157.9 (C4,6-pyrimidine), 162.7 (C=N), 173.4 (C2-pyrimidine), 179.4 (C=O); Anal. Calcd for C$_{19}$H$_{15}$N$_5$OS: C, 63.14; H, 4.18; N, 19.38; S, 8.87; Found: C, 63.59; H, 4.25; N, 19.66; S, 9.15; Anal. Calcd for C$_{19}$H$_{15}$N$_5$OS$_2$C$_4$H$_6$O$_6$: C, 49.02; H, 4.11; N, 1059; S, 4.85; Found: C, 49.21; H, 3.91; N, 10.61; S, 4.84. The synthetic scheme for production of compounds 108, 109, and 112 is set out in FIG. 9.

N-(2'-Aminopyrimidin-4'-yl)-2-(2",4"-dioxothiazolidin-5"-yl)acetamide 117: A mixture of 2,4-thiazolidinedione acetic acid 116 (10 mmol, 1.77 g) and N,N'-dicyclohexylcarbodiimide (DCC) (11.0 mmol, 2.26 g) was stirred in DMF (30 ml) at 0° C. for 30 min. To this mixture, 2,4-diaminopyrimidine (10.0 mmol, 1.1 g) was added with stirring at room temperature. The progress of the reaction was monitored by TLC and it completed after 6.5 h. The reaction mixture was diluted with ethyl acetate (60 ml), solid mass formed and filtered. The filtrate was washed successively with HCl (2.0 M), aqueous sodium carbonate and brine solution. The organic layer was removed under vacuum and the residue was purified using column employing mobile phase, ethyl acetate and petroleum ether (7:3) to afford 117 as light yellow powder, yield 76%; mp 209° C.; IR (KBr, cm$^{-1}$): 3492, 3454 (NH$_2$), 3344 (NH TZD), 3269 (NH-sec.amine linkage), 3088 (C—H, aromatic), 2931 (C—H aliphatic), 1714 (C=O), 1529 (C=N); $^1$H-NMR [DMSO-d$_6$, 400 MHz]: (δ, ppm) 2.93-3.00 (m, 1H, CH$_2$), 3.13-3.17 (m, 1H, CH$_2$), 3.88 (t, 1H, CH-thiazolidionedione), 4.58 (d, 1H, H5-pyrimidine, J=6.0 Hz), 5.60 (2H, NH$_2$, exchanges with D$_2$O), 6.93 (bs, 1H, NH, exchanges with D$_2$O), 8.34 (d, 1H, H$_6$-pyrimidine, J=6.0 Hz), 11.94 (s, 1H, NH, exchanges with D$_2$O); $^{13}$C-NMR [DMSO-d$_6$, 100 MHz]: (δ, ppm) 33.8 (CH$_2$), 53.7 (CH$_2$), 95.9 (C5-pyrimidine), 153.1 (C4-pyrimidine), 157.0 (C6-pyrimidine), 161.0 (C2-pyrimidine), 166.9 (C=O), 173.5 (C=O), 176.4 (C=O); Anal. Calcd for C$_9$H$_9$N$_5$O$_3$S: C, 40.45; H, 3.39; N, 26.20; S, 12.00; Found: C, 40.90; H, 3.46; N, 26.48; S, 12.28; Anal. Calcd for C$_9$H$_9$N$_5$O$_3$S$_2$C$_4$H$_6$O$_6$: C, 35.98; H, 3.73; N, 12.34; S, 5.65; Found: C, 36.17; H, 3.53; N, 12.33; S, 5.66.

Figure 10:
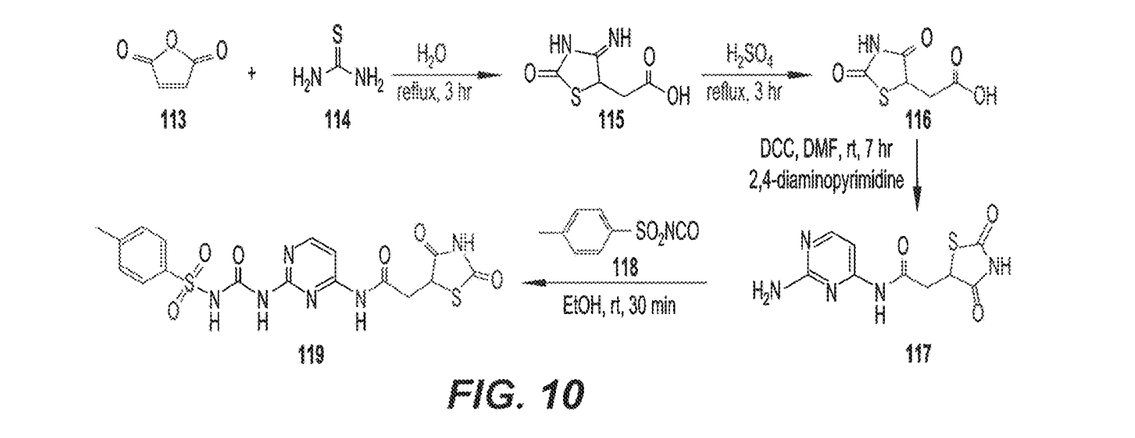
FIG. 10 depicts the synthetic scheme for compounds 115, 116, 117, and 119.

2-(2',4'-Dioxothiazolidin-5-yl)-N-[2"-(p-tosylureido)pyrimidin-4"-yl]acetamide 119: To a solution of N-(2'-aminopyrimidin-4'-yl)-2-(2",4"-dioxothiazolidin-5"-yl)acetamide 117 (10.0 mmol, 5.6 g) in absolute ethanol (30 ml), p-toluenesulfonyl isocyanate 118 (10.0 mmol, 1.52 ml) added and the resulted mixture was stirred at room temperature for 30 min. The precipitate was filtered, dried, and crystallized from appropriate solvent to yield 119 as pure product; off-white powder, yield 72%; mp 202° C.; IR (KBr, cm$^{-1}$): 3536 (NH TZD), 3325 (NH-sec. amine), 3032 (C—H, aromatic), 928 (C—H aliphatic), 1717 (C=O), 1573 (C=N); $^1$H-NMR [DMSO-d$_6$, 400 MHz]: (δ, ppm) 2.34 (s, 1H, CH$_3$), 2.70 (m, 1H, CH$_2$), 2.99 (m, 1H, CH$_2$), 4.15 (m, 1H, H5-thiazolidionedione), 5.54-5.56 (d, 1H, H5-pyrimidine, J=6.0 Hz), 5.99 (bs, 1H, NH, exchanges with D$_2$O), 7.25 (d, 2H, aromatic, J=8.0 Hz), 7.35 (d, 2H, aromatic, J=8.0 Hz), 7.67 (d, 1H, H6-pyrimidine, J=6.0 Hz), 8.03 (bs, 1H, NH, exchanges with D$_2$O), 10.20 (s, 1H, NH, exchanges with D$_2$O), 11.90 (s, 1H, NH, exchanges with D$_2$O); $^{13}$C-NMR [DMSO-d$_6$, 100 MHz]: (δ, ppm) 25.7 (CH$_3$), 33.8 (CH$_2$), 47.9 (CH$_2$), 104.3 (C5-pyrimidine), 126.0, 129.7, 141.8, 142.3 (aromatic carbon), 148.1 (C4-pyrimidine), 151.1 (C=O), 156.3 (C6-pyrimidine), 157.0 (C2-pyrimidine), 166.6 (C=O), 170.6 (C=O), 179.9 (C=O); Anal. Calcd for C$_{17}$H$_{16}$N$_6$O$_6$S$_2$: C, 43.96; H, 3.47; N, 18.09; S, 13.81; Found: C, 44.41; H, 3.54; N, 18.37; S, 14.09. The synthetic scheme for production of compounds 115, 116, 117, and 119 is set out in FIG. 10.

2,4-Dichlorothiazole-5-carbaldehyde 120: 2,4-Dichlorothiazole-5-carbaldehyde 120 was synthesized by the mixing of N,N-dimethylformamide (0.042 mol, 3.2 ml) and a suspension of 2,4-TZD 101 (0.042 mol, 4.9 g) in phosphoryl chloride (0.258 mol, 24 ml), the reaction mixture was irradiated in the microwave reactor at 100° C. for 20 min to afford 120 in 64% yield, m.p 49° C.

Figure 11:
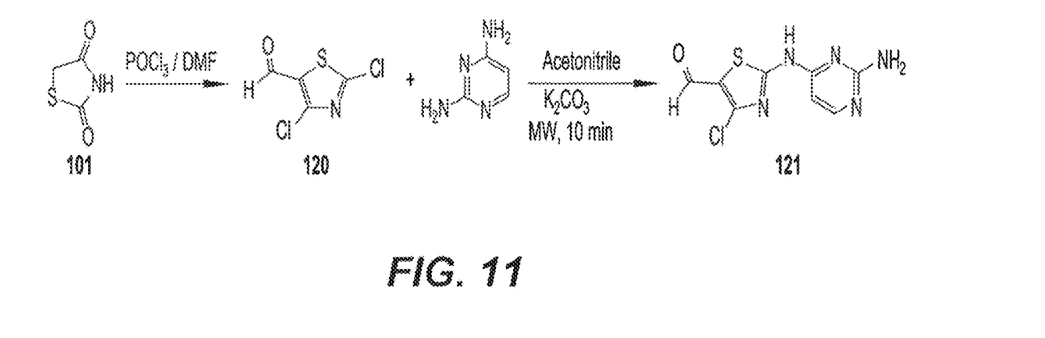
FIG. 11 depicts the synthetic scheme for compounds 120 and 121.

2-[(2'-Aminopyrimidin-4'-yl)amino]-4-chlorothiazole-5-carbaldehyde 121: To a stirred suspension of 2,4-dichlorothiazole-5-carbaldehyde 120 (0.001 mol, 0.18 g) and potassium carbonate (0.001 mol, 0.14 g) in acetonitrile (5.0 ml), 2,4-diaminopyrimidine (0.001 mol, 0.09 ml) was heated under microwave irradiation at 90-110° C. for 10 min. The formed product was purified by silica gel column chromatography using hexane:dichloromethane (1:1) as eluent to produce 121 as brown powder, yield 74%; mp 310° C.; IR (KBr, cm$^{-1}$): 3463, 3415 (NH$_2$), 3344 (NH TZD), 3207 (NH-sec.amine linkage), 3058 (C—H, aromatic), 1673 (C=O), 1499 (C=N); $^1$H-NMR [DMSO-d$_6$, 400 MHz]: (δ, ppm) 5.92 (d, 1H, H5-pyrimidine, J=6.0 Hz), 7.45 (bs, 1H, NH, exchanges with D$_2$O), 7.53-7.59 (bs, 2H, NH$_2$, exchanges with D$_2$O), 8.43 (d, 1H, H6-pyrimidine, J=6.0 Hz), 9.90 (s, 1H, CHO); $^{13}$C-NMR [DMSO-d$_6$, 100 MHz]: (δ, ppm) 99.6 (C5-pyrimidine), 126.7 (C2'-thiazole), 136.3 (C3'-thiazole), 143.8 (C6-pyrimidine), 153.4 (C5'-thiazole), C4-pyrimidine), 160.1 (C2-pyrimidine), 161.3 (C4-pyrimidine), 183.9 (CHO); Anal. Calcd for C$_8$H$_6$ClN$_5$OS: C, 37.58; H, 2.37; N, 27.39; S, 12.54; Found: C, 38.03; H, 2.44; N, 27.67; S, 12.82. The synthetic scheme for production of compounds 120 and 121 is set out in FIG. 11.

(E)-5-(p-Fluorobenzylidene)-thiazolidin-2,4-dione 122 was prepared using a method similar to the method used to prepare compound 103; yellow powder, yield 82%; $^1$H-NMR [DMSO-d$_6$, 400 MHz]: (δ, ppm) 7.36-7.40 (2H, m, aromatic H), 7.65-7.68 (2H, m, aromatic H), 7.80 (s, 1H, olefinic H), 9.77 (bs, 1H, NH, exchanges with D$_2$O); $^{13}$C-NMR [DMSO-d$_6$, 100 MHz]: (δ, ppm) 115.4 (aromatic Cs), 115.6 (C5-thiazolidione), 131.1, 131.3 (aromatic Cs), 142.3 (olefinic C), 163.9 (C—F), 165.4 (C=O), 176.9 (C=S).

Figure 12:
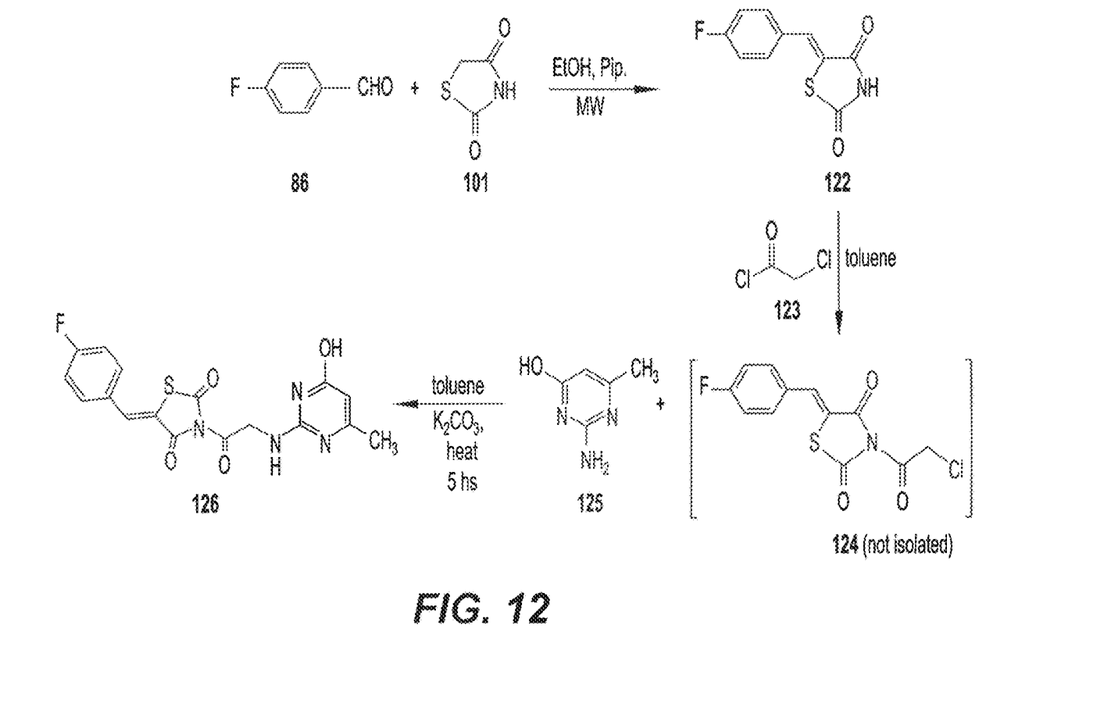
FIG. 12 depicts the synthetic scheme for compounds 122, 124, 125, and 126.

(E)-2-[5'-(p-Fluorobenzylidene)-4'-oxo-2'-thioxothiazolidin-3'-yl]-N-(4"-hydroxy-6"-methyl-pyrimidin-2"-yl)acetamide 126: 5-(p-Fluorobenzylidene)-thiazolidin-2,4-dione 122 (0.02 mol, 4.78 g) was dissolved in 50 ml of dry toluene and the solution cooled to 15° C. To the previous solution, chloroacetyl chloride 123 (0.02 mol, 1.59 ml) was added drop wise with stirring. The temperature was brought slowly to room temperature and then refluxed for 4 h. The completion of the reaction was monitored on silica gel 60 F254 precoated TLC plates by using ethyl acetate, petroleum ether and methanol (1:1:0.3). Excess of toluene was removed under reduced pressure and the solid was filtered, washed and recrystallized from ethanol to produce 124. Without isolation, 124 dissolved in 50 ml dry toluene contains freshly dried anhydrous potassium carbonate (0.0065 mol, 0.89 g) and 2-amino-6-methylpyrimidin-4-ol 125 (0.0067 mol, 0.84 g) and the reaction mixture was refluxed for 4-5 h. Excess of toluene was removed and the obtained solid washed with petroleum ether, dried and recrystallized from ethanol to afford the final product 126 as yellow powder, yield 82%; mp 292° C.; IR (KBr, cm$^{-1}$): 3358 (OH), 3332 (NH), 3013 (C—H, aromatic), 1674 (C=O), 1551 (C=N); $^1$H-NMR [DMSO-d$_6$, 400 MHz]: (δ, ppm) 3.19 (s, 3H, CH3), 3.42 (s, 2H, CH2), 5.94 (s, 1H, H5-pyrimidine), 7.90-7.11 (m, 2H, aromatic), 7.19 (olefinic H), 7.43-7.46 (m, 2H, aromatic H), 7.81 (bs, 1H, NH, exchanges with D$_2$O), 10.27 (bs, 1H, OH, exchanges with D$_2$O); $^{13}$C-NMR [DMSO-d$_6$, 100 MHz]: (δ, ppm) 26.9 (CH$_3$), 49.9 (CH$_2$), 107.1 (C5-pyrimidine), 115.4 (aromatic C), 115.7 (C5-thiazolidionedione), 131.3, 131.5 (aromatic Cs), 144.9 (C2-pyrimidine), 148.7 (olefinic C), 161.4 (C4-pyrimidine), 163.9 (C6-pyrimidine), 165.4 (C—F), 166.7 (C=O), 172.8 (C=O), 180.9 (C=S); Anal. Calcd for C$_{17}$H$_{13}$FN$_4$O$_3$S$_2$: C, 50.49; H, 3.24; N, 13.85; S, 15.86; Found: C, 50.94; H, 3.31; N, 14.31; S, 16.14. The synthetic scheme for production of compounds 122, 124, and 126 is set out in FIG. 12.

Example 3

Salt Formation

To a solution of compound 117 or compound 126 (0.1 g, 1.0 equiv.) in EtOAc (1.5 ml), a solution of L-tartaric acid (0.0215, 1.0 equiv.) in MeOH (0.2 ml) was added with continuous stirring over 1 h. The reaction mixture was stirred at room temperature for an additional 1 h. The obtained solid was collected by filtration and washed with EtOAc.

Example 4

Synthesis of Pyrimidine-Rhodanine Derivatives

To a solution of pyrimidine aldehyde 128 (0.10 mmol, 1.0 equiv.) and rhodanine/rhodanine acetic acid 129 (0.10 mmol, 1.0 equiv.) in dry CH$_2$Cl$_2$ (10.0 ml), a piperidine (0.20 mmol, 0.2 ml) was added with stirring at room temperature for 10-15 min. The solid product 130a-g was filtered and recrystallized from a mixture of acetone/water (2:1).

2-(4'-Oxo-2'-thioxothiazolidin-3'-yl)acetic acid 129: Rhodanine (0.02 mol, 4.78 g) was dissolved in 50 ml of dry toluene and the solution cooled to 15° C. To the previous solution, chloroacetic acid (0.05 M; 5.2 g in 10 ml of water) was added dropwise. After the addition was completed, the mixture was stirred at 40° C. for a period of 24 hrs. Then the excess of toluene was removed under reduced pressure. The solid was collected and recrystallized to afford 129 as a pale yellow powder, yield 81%; mp 145-148° C.; $^1$H-NMR [DMSO-d$_6$, 400 MHz]: (δ, ppm) 4.35 (s, 2H, CH$_2$, rhodanine), 4.53 (s, 2H, CH$_2$, acetyl), 7.84 (bs, 1H, OH, exchanges with D$_2$O); $^{13}$C-NMR [DMSO-d$_c$, 100 MHz]: (δ, ppm) 36.5 (C5-rhodanine), 45.2 (CH$_2$, acetyl group), 167.8 (COOH), 174.2 (C=O), 172.3 (C=O), 203.2 (C=S).

(Z)-5-[2'-(Dimethylamino)pyrimidin-5'-yl)methylene]-2-thioxothiazolidin-4-one 130a: yellow powder, yield 89%; mp 227-228° C.; IR (KBr, cm$^{-1}$): 3375 (NH), 3108 (C—H, aromatic), 2938 (aliphatic C—H), 1674 (C=O), 1599 (C=N); $^1$H-NMR [DMSO-d$_6$, 400 MHz]: (δ, ppm) 3.15 (s, 6H, CH$_3$), 7.43 (s, 1H, olefinic H), 8.57 (s, 2H, H$_{4,6}$-pyrimidine), 11.07 (bs, 1H, NH, exchanges with D$_2$O); $^{13}$C-NMR [DMSO-d$_6$, 100 MHz]: (δ, ppm) 43.8 (CH$_3$), 115.9 (C5-pyrimidine), 118.1 (C5-rhodanine), 128.7 (olefinic C), 160.3 (C4,6-pyrimidine), 160.8 (C2-pyrimidine) 167.1 (C=O), 192.7 (C=S); Anal. Calcd for C$_{10}$H$_{10}$N$_4$OS$_2$: C, 45.09; H, 3.78; N, 21.04; S, 24.08; Found: C, 45.56; H, 3.85; N, 21.32; S, 24.36; Anal. Calcd for C$_{10}$H$_{10}$N$_4$OS$_2$.CH$_3$I: C, 32.36; H, 3.21; N, 13.72; S, 15.71; Found: C, 32.55; H, 3.01; N, 13.73; S, 15.70.

(Z)-5-[(2'-Aminopyrimidin-5'-yl)methylene]-2-thioxothiazolidin-4-one 130b: yellowish brown powder, yield 87%; mp 268° C.; IR (KBr, cm$^{-1}$): 3513, 3480 (NH$_2$), 3362 (NH), 3086 (C—H, aromatic), 1721 (C=O), 1583 (C=N); $^1$H-NMR [DMSO-d$_6$, 400 MHz]: (δ, ppm) 7.07 (s, 2H, NH$_2$, exchanges with D$_2$O), 7.84 (s, 1H, olefinic H), 8.62 (s, 2H, H$_{4,6}$-pyrimidine), 11.30 (bs, 1H, NH, exchanges with D$_2$O); $^{13}$C-NMR [DMSO-d$_6$, 100 MHz]: (δ, ppm) 117.5 (C5-pyrimidine), 122.01 (C5-rhodanine), 138.9 (olefinic C), 157.8 (C4,6-pyrimidine), 158.7 (C2-pyrimidine), 164.0 (C=O), 177.9 (C=S); Anal. Calcd for C$_8$H$_6$N$_4$OS$_2$: C, 40.32; H, 2.54; N, 23.51; S, 26.91; Found: C, 40.77; H, 2.61; N, 23.78; S, 27.19; Anal. Calcd for C$_8$H$_6$N$_4$OS$_2$.C$_4$H$_6$O$_6$: C, 37.11; H, 3.11; N, 14.43; S, 16.51; Found: C, 37.30; H, 2.91; N, 14.44; S, 16.53.

(Z)-2-[2'-(Dimethylamino)pyrimidin-5'-yl)methylene)-4-oxo-2-thioxothiazolidin-3-yl]-acetic acid 130c: yellow powder, yield 81%; mp 234° C.; IR (KBr, cm$^{-1}$): 3290 (OH), 3048 (C—H, aromatic), 2936 (aliphatic C—H), 1705 (C=O), 1409 (C=N); $^1$H-NMR [DMSO-d$_6$, 400 MHz]: (δ, ppm) 3.19 (s, 6H, CH$_3$), 4.33 (s, 2H, CH$_2$), 7.61 (s, 1H, olefinic H), 8.58 (s, 2H, H$_{4,6}$-pyrimidine), 9.60 (bs, 1H, OH, exchanges with D$_2$O); $^{13}$C-NMR [DMSO-d$_6$, 100 MHz]: (δ, ppm) 43.8 (CH$_3$), 48.4 (CH$_2$), 115.9 (C5-pyrimidine), 118.1 (C5-rhodanine), 128.7 (olefinic C), 160.3 (C4,6-pyrimidine), 160.8 (C2-pyrimidine) 167.1 (C=O), 167.8 (C=O, carboxylic acid), 192.7 (C=S); Anal. Calcd for C$_{12}$H$_{12}$N$_4$O$_3$S$_2$: C, 44.43; H, 3.73; N, 17.27; S, 19.77; Found: C, 44.88; H, 3.80; N, 17.55; S, 20.05; Anal. Calcd for C$_{12}$H$_{12}$N$_4$O$_3$S$_2$.CH$_3$I: C, 33.48; H, 3.24; N, 12.01; S, 13.75; Found: C, 33.67; H, 3.03; N, 12.03; S, 13.77.

(Z)-2-[5'-(2"-(Isopropylamino)pyrimidin-5"-yl)methylene)-4'-oxo-2'-thioxothiazolidin-3'-yl]acetic acid 130d: yellow powder, yield 86%; mp 257° C.; IR (KBr, cm$^{-1}$): 3442 (OH), 3242 (NH), 3080 (C—H, aromatic), 2865 (aliphatic C—H), 1716 (C=O), 1448 (C=N); $^1$H-NMR [DMSO-d$_6$, 400 MHz]: (δ, ppm) 1.19 (s, 6H, CH$_3$, isopropyl group), 4.12-4.17 (m, CH-isopropyl group), 4.39 (s, 1H, CH$_2$, rhodanine), 7.62 (s, 1H, olefinic H), 8.13 (d, 1H, NH, J=6.0 Hz), 8.58 (s, 2H, H$_{4,6}$-pyrimidine), 11.04 (bs, 1H, OH, exchanges with D$_2$O); $^{13}$C-NMR [DMSO-d$_6$, 100 MHz]: (δ, ppm) 22.6 (CH$_3$, isopropyl), 43.9 (CH, isopropyl), 45.4 (CH$_2$, rhodanine), 116.4 (C5-pyrimidine), 117.6 (C5-rhodanine), 129.1 (olefinic C), 160.3 (C4,6-pyrimidine), 160.9 (C2-pyrimidine) 167.1 (C=O), 167.2 (C=O, carboxylic acid), 192.7 (C=S); Anal. Calcd for C$_{13}$H$_{14}$N$_4$O$_3$S$_2$: C, 46.14; H, 4.17; N, 16.56; S, 18.95; Found: C, 46.59; H, 4.24; N, 16.84; S, 19.23; Anal. Calcd for C$_{13}$H$_{14}$N$_4$O$_3$S$_2$·C$_4$H$_6$O$_6$: C, 41.80; H, 4.13; N, 11.47; S, 13.13; Found: C, 41.99; H, 3.93; N, 11.48; S, 13.15.

(Z)-2-[5'-(2"-Morpholinopyrimidin-5"-yl)methylene)-4'-oxo-2'-thioxothiazolidin-3'-yl]-acetic acid 130e: yellow powder, yield 88%; mp 248° C.; IR (KBr, cm$^{-1}$): 3590 (OH), 3058 (C—H, aromatic), 2960 (aliphatic C—H), 1713 (C=O), 1508 (C=N); $^1$H-NMR [DMSO-d$_6$, 400 MHz]: (δ, ppm) 3.64-3.65 (m, 4H, morpholine), 3.81-3.83 (m, 4H, morpholine), 4.32 (s, 2H, CH$_2$), 7.64 (s, 1H, olefinic H), 8.63 (s, 2H, H$_{4,6}$-pyrimidine), 11.78 (bs, 1H, OH, exchanges with D$_2$O); $^{13}$C-NMR [DMSO-d$_6$, 100 MHz]: (δ, ppm) 44.5 (CH$_2$), 48.4, 66.3 (morpholine), 116.8 (C5-pyrimidine), 119.1 (C5-rhodanine), 128.2 (olefinic C), 160.2 (C4,6-pyrimidine), 160.4 (C2-pyrimidine), 167.0 (C=O), 167.1 (C=O, carboxylic acid), 192.7 (C=S); Anal. Calcd for C$_{14}$H$_{14}$N$_4$O$_4$S$_2$: C, 45.89; H, 3.85; N, 15.29; S, 17.50; Found: C, 46.34; H, 3.92; N, 15.57; S, 17.78; Anal. Calcd for C$_{14}$H$_{14}$N$_4$O$_4$S$_2$·CH$_3$I: C, 35.44; H, 3.37; N, 11.02; S, 12.62; Found: C, 35.63; H, 3.18; N, 11.05; S, 12.64.

(Z)-2-{4'-Oxo-5'-[2"-(n-propylamino)pyrimidin-5"-yl)methylene]-2'-thioxothiazolidin-3'-yl}acetic acid 130f: White powder, yield 83%; mp 244° C.; IR (KBr, cm$^{-1}$): 3545 (OH), 3253 (NH), 3120 (C—H, aromatic), 2951 (aliphatic C—H), 1715 (C=O), 1450 (C=N); $^1$H-NMR [DMSO-d$_6$, 400 MHz]: (δ, ppm) 0.87 (s, 3H, CH$_3$, propyl group), 2.89 (s, 4H, 2CH$_2$, propyl group), 4.34 (s, CH$_2$, rhodanine), 7.57 (s, 1H, olefinic H), 8.20 (s, 1H, NH, exchanges with D$_2$O), 8.50 (s, 2H, H$_{4,6}$-pyrimidine), 9.23 (bs, 1H, OH, exchanges with D$_2$O); $^{13}$C-NMR [DMSO-d$_6$, 100 MHz]: (δ, ppm) 11.8 (CH$_3$, propyl), 22.7 (CH$_2$, propyl), 43.8 (CH$_2$, propyl), 48.3 (CH$_2$, rhodanine), 116.5 (C5-pyrimidine), 117.8 (C5-rhodanine), 128.9 (olefinic C), 160.8 (C4,6-pyrimidine), 161.8 (C2-pyrimidine), 167.1 (C=O), 167.8 (C=O, carboxylic acid), 192.7 (C=S); Anal. Calcd for C$_{13}$H$_{14}$N$_4$O$_3$S$_2$: C, 46.14; H, 4.17; N, 16.56; S, 18.95; Found: C, 46.59; H, 4.24; N, 16.84; S, 19.23; Anal. Calcd for C$_{13}$H$_{14}$N$_4$O$_3$S$_2$·C$_4$H$_6$O$_6$: C, 41.80; H, 4.13; N, 11.47; S, 13.13; Found: C, 41.98; H, 3.94; N, 11.48; S, 13.14.

Figure 13:
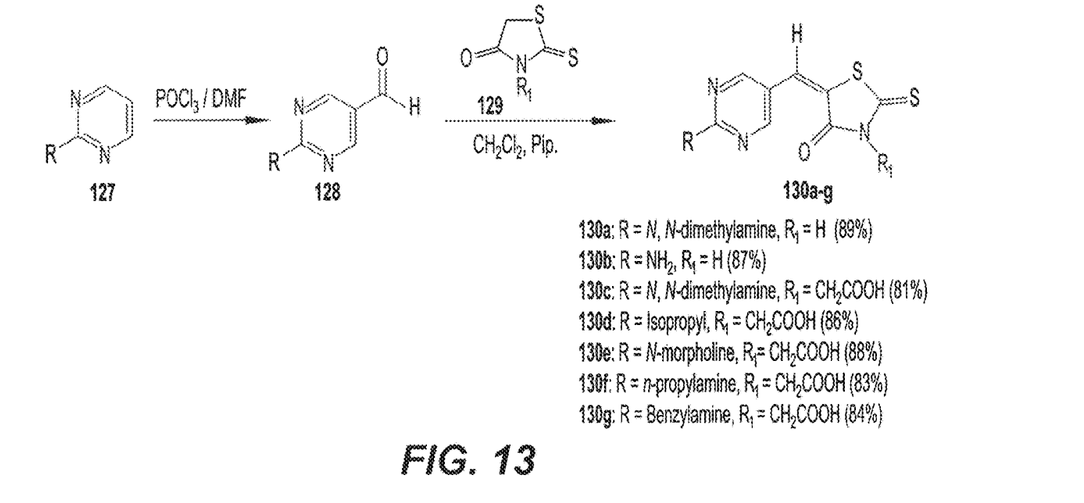
FIG. 13 depicts the synthetic scheme for compounds 128 and 130a-g.

(Z)-2-{5'-[2"-(Benzylamino)pyrimidin-5"-yl]methylene-4'-oxo-2'-thioxothiazolidin-3'-yl}acetic acid 130g: yellow powder, yield 84%; mp 233° C.; IR (KBr, cm$^{-1}$): 3581 (OH), 3244 (NH), 3111 (C—H, aromatic), 2944 (aliphatic C—H), 1708 (C=O), 1524 (C=N); $^1$H-NMR [DMSO-d$_6$, 400 MHz]: (δ, ppm) 4.31 (s, 2H, CH$_2$, rhodanine), 4.57 (d, 2H, CH$_2$, benzylamine, J=6.3 Hz), 7.20-7.29 (m, 5H, aromatic H), 7.60 (s, 1H, olefinic H), 8.58 (s, 2H, H$_{4,6}$-pyrimidine), 8.70 (s, 1H, NH, exchanges with D$_2$O), 9.13 (bs, 1H, OH, exchanges with D$_2$O); $^{13}$C-NMR [DMSO-d$_6$, 100 MHz]: (δ, ppm) 3.9 (CH$_2$, rhodanine), 48.5 (CH$_2$, benzylamine), 117.1 (C5-pyrimidine), 118.4 (C5-rhodanine), 127.3, 127.5, 128.6, 128.8 (aromatic), 139.8 (olefinic C), 160.8 (C4,6-pyrimidine), 161.8 (C2-pyrimidine), 167.2 (C=O), 167.4 (C=O, carboxylic acid), 192.7 (C=S); Anal. Calcd for C$_{17}$H$_{14}$N$_4$O$_3$S$_2$: C, 52.84; H, 3.65; N, 14.50; S, 16.59; Found: C, 53.29; H, 3.72; N, 14.78; S, 16.87; Anal. Calcd for C$_{17}$H$_{14}$N$_4$O$_3$S$_2$·C$_4$H$_6$O$_6$: C, 47.01; H, 3.76; N, 10.44; S, 11.95; Found: C, 47.20; H, 3.56; N, 10.46; S, 11.97. The synthetic scheme for production of compounds 130a-g is set out in FIG. 13.

Example 5

Synthesis of Pyrimidine-Oxadiazoles 134a-c

General Procedure for Synthesis of 1,3,4-oxadiazole Derivatives

Figure 14:
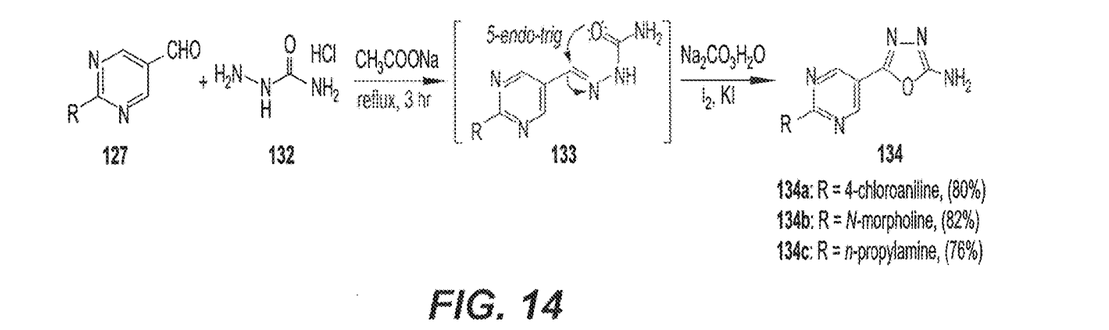
FIG. 14 depicts the synthetic scheme for compounds 134a-c.

A mixture of pyrimidine aldehyde 131 (0.03 mol) and semicarbazide HCl 132 (0.05 mol) in ethanol (20 ml) was refluxed for 3 hours at 100° C. The solvent was distilled off and the solid mass obtained was used in the next step without further purification. The solid mass (0.01 mol) and sodium carbonate (0.01 mol) was dissolved in water (25 ml). To the previous mixture, iodine (0.01 mol) and potassium iodide (0.01 mol) were added and the reaction mixture refluxed for 2 hours at 100° C. The reaction mixture was then allowed to cool; the solid produced was filtered, washed with water and recrystallized from methanol to give 134a-c. The synthetic scheme for production of compounds 134a-134c is set out in FIG. 14.

5-{2'-[p-Chlorophenyl)amino]pyrimidin-5'-yl}-1,3,4-oxadiazol-2-amine 134a: yellow crystals; yield 80%; mp 282° C.; IR (KBr, cm$^{-1}$): 3309, 3113 (NH$_2$), 1666 (C=N), 1589 (C=C); $^1$H-NMR [DMSO-d$_6$, 400 MHz]: (δ, ppm) 7.55 (bs, 2H, NH$_2$, exchangeable with D$_2$O), 7.64 (d, 2H, aromatic, J=8.0 Hz), 8.43 (d, 2H, aromatic, J=8.0 Hz), 9.24 (s, 2H, H$_{4,6}$-pyrimidine), 12.88 (bs, 1H, NH exchangeable with D$_2$O); $^{13}$C-NMR [DMSO-d$_6$, 100 MHz]: (δ, ppm) 117.9 (C5-pyrimidine), 129.5-136.9 (aromatic), 153.9 (C4,6-pyrimidine), 154.3 (C2-pyrimidine), 163.1 (C2-oxadiazole), 164.9 (C4-oxadizole); Anal. Calcd for C$_{12}$H$_9$ClN$_6$O: C, 49.92; H, 3.14; N, 29.11; Found: C, 50.37; H, 4.93; N, 34.13; Anal. Calcd for C$_{12}$H$_9$ClN$_6$O·2C$_4$H$_6$O$_6$: C, 40.79; H, 3.59; N, 14.27; Found: C, 40.98; H, 3.40; N, 14.28.

5-(2'-Morpholinopyrimidin-5'-yl)-1,3,4-oxadiazol-2-amine) 134b: off-white crystals; yield 82%; mp 263° C.; IR (KBr, cm$^{-1}$): 3457, 3274 (b, NH$_2$), 2954 (C—H aliphatic), 1662 (C=N), 1600 (C=C); $^1$H-NMR [DMSO-d$_6$, 400 MHz]: (δ, ppm) 3.66-3.79 (m, 8H, morpholine), 6.49 (bs, 2H, NH$_2$, exchangeable with D$_2$O), 8.73 (s, 2H, H$_{4,6}$-pyrimidine); $^{13}$C-NMR [DMSO-d$_6$, 100 MHz]: (δ, ppm) 44.4 (morpholine), 66.4 (morpholine), 118.4 (C5-pyrimidine), 135.3 (C4,6-pyrimidine), 156.6 (C2-pyrimidine), 157.2 (C2-oxadiazole), 161.2 (C4-oxadizole); Anal. Calcd for C$_{10}$H$_{12}$N$_6$O$_2$: C, 48.38; H, 4.87; N, 33.85; Found: C, 48.83; H, 4.94; N, 34.10; Anal. Calcd for C$_{10}$H$_{12}$N$_6$O$_2$·C$_4$H$_6$O$_6$: C, 42.21; H, 4.55; N, 21.10; Found: C, 42.40; H, 4.37; N, 21.11.

5-[2'-(n-Propylamino)pyrimidin-5'-yl]-1,3,4-oxadiazol-2-amine 134c: white crystals; yield 76%; mp 211° C.; IR (KBr, cm$^{-1}$): 3464, 3442 (NH$_2$), 3256 (NH), 2957 (C—H aliphatic), 1673 (C=N), 1528 (C=C); $^1$H-NMR [DMSO-d$_6$, 400 MHz]: (δ, ppm) 0.86-0.9 (m, 3H, CH$_3$), 1.49-1.58 (m, 2H, CH$_2$), 3.22-3.25 (m, 2H, CH$_2$), 6.46 (bs, 2H, NH$_2$, exchangeable with D$_2$O), 7.89 (s, 1H, NH, exchangeable with D$_2$O), 8.63 (s, 2H, H$_{4,6}$-pyrimidine); $^{13}$C-NMR [DMSO-d$_6$, 100 MHz]: (δ, ppm) 11.9 (CH$_3$, propyl), 22.6 (CH$_2$, propyl), 42.9 (CH$_2$, propyl), 117.8 (C5-pyrimidine), 135.8 (C4,6-pyrimidine), 157.3 (C2-pyrimidine), 162.4 (C2-oxadiazole), 163.7 (C4-oxadizole); Anal. Calcd for C$_9$H$_{12}$N$_6$O: C, 49.08; H, 5.49; N, 38.16; Found: C, 49.53; H, 5.56; N, 38.44; Anal. Calcd for C$_9$H$_{12}$N$_6$O·2C$_4$H$_6$O$_6$: C, 39.24; H, 4.65; N, 16.15; Found: C, 39.43; H, 4.46; N, 16.18.

Example 6

Synthesis of Pyrimidine-Imidazolidin-2,4-dione 138

(E)-2-(p-Fluorobenzylidene)hydrazinecarboxamide 135: A mixture of p-fluorobenzaldehyde 86 (0.01 mol, g) and semicarbazide HCl 132 (0.02 mol) in ethanol (20 ml) was refluxed for 3 hours at 100° C. The solvent was removed under reduced pressure and the solid recrystallized and collected by filtration to produce 135 as a white powder; yield 93%; mp 232° C.; $^1$H-NMR [DMSO-d$_6$, 400 MHz]: (δ, ppm) 6.49 (bs, 2H, NH$_2$, exchangeable with D$_2$O), 7.18 (m, 2H, aromatic), 7.74 (m, 2H, aromatic), 7.80 (s, 1H, olefinic H), 10.22 (bs, 1H, NH exchangeable with D$_2$O); $^{13}$C-NMR [DMSO-d$_6$, 100 MHz]: (δ, ppm) 116.1-131.8 (aromatic C), 138.7 (olefinic C), 157.3 (C=O), 164.2 (C—F).

(E)-3-[(p-Fluorobenzylidene)amino]imidazolidine-2,4-dione 137: A mixture of 2-(p-fluorobenzylidene)hydrazinecarboxamide 135 (0.01 mol, 2.2 g), ethyl chloroacetate 136 (0.01 mol, 1.1 ml) and fused sodium acetate (0.1 mol, 0.8 g) in ethanol was heated under reflux for 2 h. The reaction mixture was allowed to cool to room temperature and the mixture poured into an ice water bath. The solid was collected by filtration and recrystallized to afford 137 as a white powder in yield 87%, mp 224° C.; $^1$H-NMR [DMSO-d$_6$, 400 MHz]: (δ, ppm) 4.34 (CH$_2$), 7.20-7.25 (2H, m, phenyl), 7.78-7.80 (2H, m, phenyl), 7.84 (s, 1H, olefinic H), 10.27 (1H, bs, NH exchangeable with D$_2$O); $^{13}$C-NMR [DMSO-d$_6$, 100 MHz]: (δ, ppm) 42.9 (CH$_2$), 129.0-135.8 (aromatic C), 156.6 (olefinic C), 157.3 (C=O), 162.4 (C—F), 163.7 (C=O).

Figure 15:
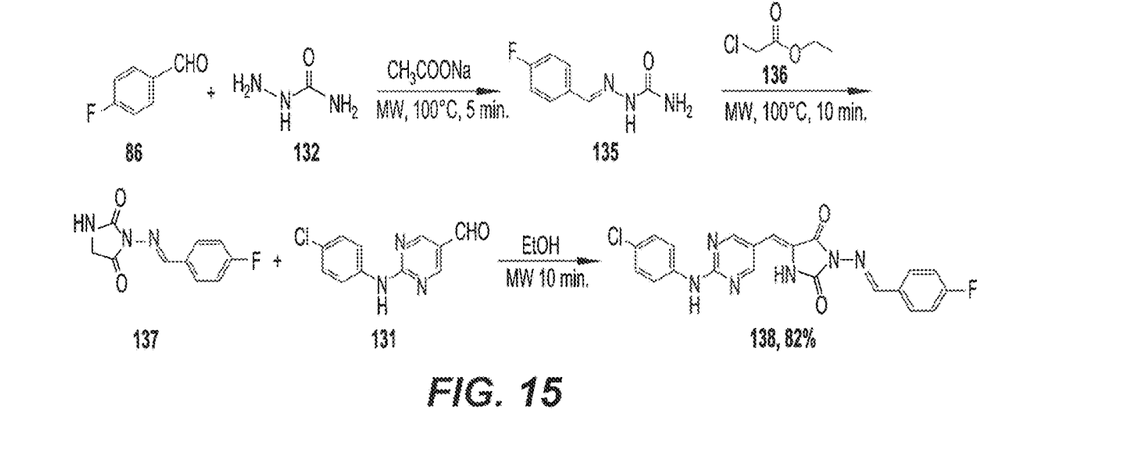
FIG. 15 depicts the synthetic scheme for compounds 135, 137, and 138.

(Z)-5-{2'-[p-Chlorophenylamino)pyrimidin-5'-yl]methylene}-3-(E)-(p-fluoro-benzylidene amino)imidazolidine-2,4-dione 138: A mixture of (E)-3-[(p-fluoro-benzylidene)amino] imidazolidine-2,4-dione 137 (0.1 mmol, 0.02 g), and pyrimidine aldehyde 131 (0.1 mmol, 0.02 g) in ethanol was heated under microwave irradiation. The reaction mixture was allowed to cool to room temperature. The solid obtained was filtered-off and recrystallized from ethanol to give 138 as yellow powder; yield 85%; mp 226° C.; IR (KBr, cm$^{-1}$): 3411 (NH), 1687 (C=O), 1600 (C=N); $^1$H-NMR [DMSO-d$_6$, 400 MHz]: (δ, ppm) 7.18 (m, 2H, p-fluorophenyl), 7.41 (s, 1H, olefinic H), 7.57 (d, 2H, p-chlorophenyl, J=8.0 Hz), 7.69 (bs, 1H, NH, exchangeable with D$_2$O), 7.77 (m, 2H, p-fluorophenyl), 7.82 (s, 1H, olefinic H), 8.35 (d, 2H, p-chlorophenyl, J=8.0 Hz), 8.93 (s, 2H, H$_{4,6}$-pyrimidine), 10.25 (bs, 1H, NH, exchangeable with D$_2$O); $^{13}$C-NMR [DMSO-d$_6$, 100 MHz]: (δ, ppm) 126.9-139.7 (aromatic C), 153.9 (C=O), 155.3 (C4,6-pyrimidine), 157.1 (olefinic C), 158.6 (C=O), 160.7 (C—F), 162.1 (C2-pyrimidine); Anal. Calcd for C$_{21}$H$_{14}$ClFN$_6$O$_2$: C, 57.74; H, 3.23; N, 19.24; Found: C, 58.0; H, 3.31; N, 19.33. The synthetic scheme for production of compounds 135, 137, and 138 is set out in FIG. 15.

It is to be understood that the pyrimidine-thiazolidinone derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A pyrimidine-thiazolidinone derivative, comprising a compound selected from the group consisting of:

and a pharmaceutically acceptable salt thereof, wherein
X is selected from the group consisting of N—CH$_3$ and 0;
Ar is selected from the group consisting of 2, 4-diaminopyrimidine, and 2-chloro-4-aminopyrimidine; and
R is selected from the group consisting of 4-chloroaniline, NH$_2$, N,N-dimethylamine, isopropyl, N-morpholine, n-propylamine, and benzylamine;
R$_1$ is selected from the group H and CH$_2$COOH.

2. The pyrimidine-thiazolidinone derivative as recited in claim 1, wherein the compound is or a pharmaceutically acceptable salt thereof.

3. The pyrimidine-thiazolidinone derivative as recited in claim 1, wherein the pharmaceutically acceptable salt is

4. The pyrimidine-thiazolidinone derivative as recited in claim 1, wherein the compound is

105b or a pharmaceutically acceptable salt thereof.

5. The pyrimidine-thiazolidinone derivative as recited in claim 1, wherein the compound is

126 or a pharmaceutically acceptable salt thereof.

6. A pharmaceutical composition, comprising: a therapeutically effective amount of the compound of claim 1 and a pharmaceutically acceptable excipient.

7. A method of treating type-2 diabetes, comprising administering a therapeutically effective amount of the compound of claim 1 to a patient in need thereof.

8. The method as recited in claim 7, wherein the compound is or a pharmaceutically acceptable salt thereof.

9. The method as recited in claim 8, wherein the pharmaceutically acceptable salt is

10. The method as recited in claim 7, wherein the compound is

105b or a pharmaceutically acceptable salt thereof.

11. The method as recited in claim 7, wherein the compound is

126 or a pharmaceutically acceptable salt thereof.

* * * * *